United States Patent [19]

Grollier et al.

[11] 4,304,563

[45] Dec. 8, 1981

[54] COMPOSITION AND PROCESS FOR THE TREATMENT OF KERATINIC MATERIALS BASED ON FLUORINE DERIVATIVES

[75] Inventors: Jean F. Grollier; Claire Fiquet, both of Paris; Claude Dubief, Versailles; Chantal Fourcadier, Paris; Daniele Cauwet, Crosne, all of France

[73] Assignee: Société Anonyme dite: L'Oreal, Paris, France

[21] Appl. No.: 74,768

[22] Filed: Sep. 11, 1979

[30] Foreign Application Priority Data

Feb. 27, 1979 [FR] France .................................. 79 05068

[51] Int. Cl.³ ............................................... A61K 7/06
[52] U.S. Cl. ...................................... 8/127.51; 424/70
[58] Field of Search ............... 424/70; 8/127.51, 127.5

[56] References Cited

U.S. PATENT DOCUMENTS

| | | | |
|---|---|---|---|
| 3,993,745 | 11/1976 | Cella et al. | 424/71 |
| 4,013,786 | 3/1977 | Cella et al. | 424/70 |
| 4,059,688 | 11/1977 | Rosenberg et al. | 424/71 |
| 4,183,367 | 1/1980 | Goebel | 424/70 |

FOREIGN PATENT DOCUMENTS

| | | | |
|---|---|---|---|
| 2054478 | 4/1971 | France | 424/70 |
| 2387648 | 11/1978 | France . | |
| 1312675 | 4/1973 | United Kingdom | 424/70 |

Primary Examiner—Ethel G. Love
Attorney, Agent, or Firm—Cushman, Darby & Cushman

[57] ABSTRACT

The invention relates to compositions based on a cationic polymer and a fluorine derivative for the treatment of keratinic material. The cationic polymer is a substantive polymer and the fluorine derivative has the formula Gf—Z or (Gf—O)$_2$—PO$_2$H wherein Z represents —COOH, —SO$_3$H, —OSO$_3$H, —OPO$_2$H and —OPO$_3$H$_2$ and Gf represents

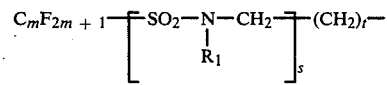

wherein m ranges from 1 to 20, s is equal to 0 or 1, t ranges from 0 to 20 and R$_1$ is alkyl having 1-20 carbon atoms. These compositions permit principally to remedy for a prolonged period of time the problem of the re-appearance of an oily appearance of hair.

9 Claims, No Drawings

COMPOSITION AND PROCESS FOR THE TREATMENT OF KERATINIC MATERIALS BASED ON FLUORINE DERIVATIVES

The present invention relates to a cosmetic composition for treating keratinic materials and, in particular, for treating the hair and skin, the said composition being based on a fluorine derivative.

It is known that compositions containing fluorine derivatives have been used, principally to shorten the time for drying hair. However, it has now been discovered that, in accordance with the present invention, the use of certain fluorine derivatives having an anionic character in combination with substantive cationic polymers provides particularly valuable results in the treatment of keratinic material and, in particular, in the treatment of the hair and skin. More particularly, the use of these compounds in compositions for the treatment of hair essentially eliminates the oily appearance of hair and significantly retards or delays the recurrence of this oily appearance while at the same time imparts to the hair softness, flexibility and ease of combing.

It has also been noted in accordance with the present invention that the combination of the fluorine derivative with a substantive cationic polymer improves the coupling of these fluorine derivatives having an anionic character to the keratinic material.

This combination of components is particularly interesting in processes for treating the hair or skin which include, after application thereto, a rinsing operation. Heretofore a rinsing operation has at times been considered disadvantageous since it removes a significant amount of compounds applied, for instance, to the hair, which compounds, however, were only difficultly fixed to the keratinic material. The present invention, however, also resolves this problem.

The present invention thus relates to a composition for use in the treatment of keratinic materials containing at least one fluorine derivative and a substantive cationic polymer. The present invention also relates to a process for fixing the said fluorine derivative on the hair or skin by means of a cationic polymer.

The composition of the present invention, for use in the treatment of keratinic materials, comprises in an aqueous medium:

(a) at least one fluorine derivative of the formula:
$$GF—Z \text{ or } (Gf—O)_2PO_2H$$

wherein Z represents $-COOH$, $-SO_3H$, $-OSO_3H$, $-OPO_2H$ or $-OPO_3H_2$, and
Gf represents

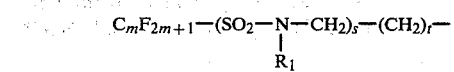

wherein m ranges from 1 to 20, s is equal to 0 or 1, t ranges from 0 to 20 and $R_1$ represents alkyl having 1–20 carbon atoms, with the proviso that when the fluorine derivative has the formula, $(Gf-O)_2-PO_2H$, the Gf moieties can be identical or different, and the cosmetically acceptable salts thereof; and (b) at least one substantive cationic polymer.

Representative fluorine derivatives usefully employed in the present invention include:

$C_7F_{15}-COOH$; $C_8F_{17}-CH_2-COOH$; $C_8F_{17}-SO_3H$,

-continued

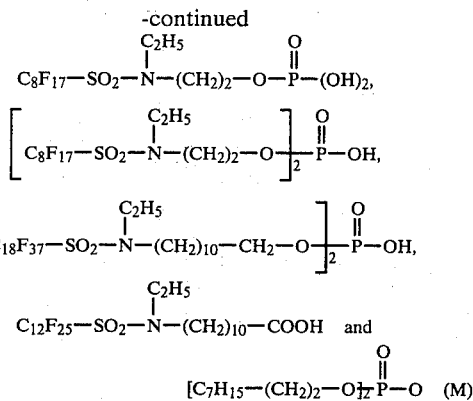

$$C_{12}F_{25}-SO_2-\underset{\underset{C_2H_5}{|}}{N}-(CH_2)_{10}-COOH \text{ and}$$

$$[C_7H_{15}-(CH_2)_2-O]_{\overline{2}}\overset{O}{\underset{\|}{P}}-O \quad (M)$$

wherein M is an alkali metal or $NH_4^\oplus$, as well as products sold under the trade names ZONYL by E. I. duPont de Nemours, FLUORAD FC and SCOTCHBAN FC by 3M, and FORAFAC by Ungine Kuhlmann.

Preferably the salts of these fluroine derivatives used in accordance with the present invention are ammonium salts and alkali metal salts such as sodium or potassium salts.

The term substantive cationic polymer in the context of the present invention means a cationic polymer containing a significant number of tertiary amine or quaternary amine groups and having a molecular weight between 500 and about 5,000,000. These cationic polymers provide red color which is more intense than the control in the Rouge Supracide 3B test.

This test employs a 1% aqueous solution of Rouge Supracide 3B (C.I. Acid Red 35) adjusted to pH 5 by HCl.

A one gram sample of bleached hair is immersed in 5 cm³ of a 1% aqueous solution of the polymer being tested at pH 7, for ten minutes at ambient temperature.

After rinsing the hair sample with water, it is then dried for 30 minutes at 60° C.

The hair sample is then plunged into 20 cm³ of the Rouge Supracide 3B solution for 5 minutes at 20° C. Thereafter, the hair sample is rinsed and then dried for 30 minutes at 60° C.

The "control" used in this test is a hair sample which has not previously been treated with the solution of the polymer being tested.

The substantivity of the cationic polymer can also be treated or measured by taking up its weight in accordance with the following procedure:

A 0.5 g sample of bleached hair is weighed after having been placed in a dessicator for 24 hours (Po).

The sample is then washed and rinsed. After drying, it is immersed in 2 cm³ of a 3% aqueous solution of polymer being tested for 10 minutes. After rinsing with water, the sample is then dried for 30 minutes at 60° C. This operation is repeated four times. Thereafter, the hair sample is placed in a dessicator for 24 hours. The hair sample is then weighed (P). The take up of weight is then determined by the formula:

$$\Delta P\% = [(P-Po)/Po] \times 100$$

A substantive polymer is one whose $\Delta P$ is greater than 0.5%.

Representative cationic polymers include:

(1) water-soluble cyclopolymers having a molecular weight of 20,000 to 3,000,000, including homopolymers having in the principal chain thereof units having formula II or II':

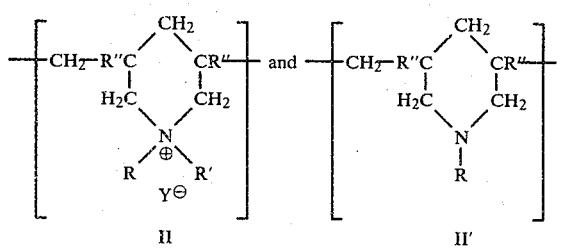

wherein R'' represents hydrogen or methyl,

R and R' each independently represent alkyl having 1-22 carbon atoms, hydroxyalkyl wherein the alkyl moiety has, preferably, 1-5 carbon atoms and amido lower alkyl, or R and R' together with the nitrogen atom to which they are attached can form a heterocycle such as piperidinyl or morpholinyl, and $Y^\ominus$ is an anion, such as bromide, chloride, acetate, borate, citrate, tartrate, bisulfate, bisulfate, sulfate and phosphate. Further copolymers of acrylamide or diacetone acrylamide having units of Formula II or II' can also be employed in the present invention.

Representative quanternary ammonium polymers of the type defined above, which are those more particularly preferred for use in the present invention include the homopolymer of dimethyl diallyl ammonium chloride solid under the trade name MERQUAT 100 having a molecular weight lower than 100,000 and the copolymer of dimethyl diallyl ammonium chloride and acrylamide, having a molecular weight greater than 500,000 and sold under the name MERQUAT 500.

These polymers are described in French Pat. No. 2,080,759 and its certificate of addition No. 2,190,406;

(2) quaternary polyammoniums of the formula

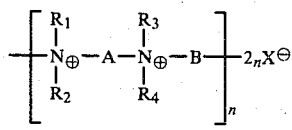

wherein $R_1$, $R_2$, $R_3$ and $R_4$ each independently represent an aliphatic, alicyclic or arylaliphatic radical containing a maximum of 20 carbon atoms, or a lower hydroxy aliphatic radical, or the pairs $R_1$ and $R_2$, and $R_3$ and $R_4$, both or individually, together with the nitrogen atom to which these respective pairs of substituents are attached form heterocycles containing, optionally, a second heteroatom other than nitrogen, or $R_1$, $R_2$, $R_3$ and $R_4$ represent

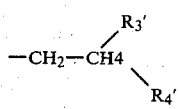

wherein $R'_3$ represents hydrogen or lower alkyl and $R'_4$ represents

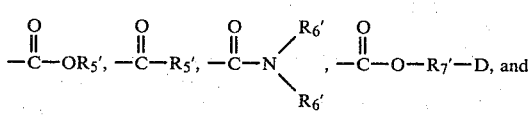

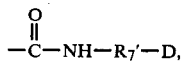

wherein $R'_5$ represents lower alkyl, $R'_6$ represents hydrogen or lower alkyl, $R'_7$ represents alkylene and D represents a quaternary ammonium group;

A and B can represent a linear or branched, saturated or unsaturated polymethylene group containing from 2 to 20 carbon atoms, or a said polymethylene group having interposed in its principal chain one or more groups such as

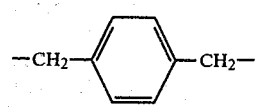

and —$CH_2$—Y—$CH_2$— wherein Y represents

O, S, SO or $SO_2$, —S—,

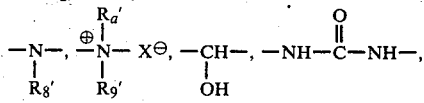

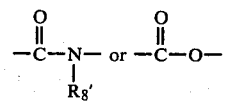

wherein $X^\ominus$ represents an anion derived from a mineral or organic acid, $R'_8$ represents hydrogen or lower alkyl, $R'_9$ represents lower alkyl or A, together with $R_1$ and $R_3$ form with the two nitrogen atoms to which $R_1$ and $R_3$ are attached a piperizine radical; further when A represents linear or branched, saturated or unsaturated alkylene or hydroxyalkylene, B can also represent —$(CH_2)_n$—CO—D—OC—$(CH_2)_n$— wherein D represents:

(a) a glycol residue of the formula —O—Z—O— wherein Z represents a linear or branched hydrocarbon or a group having one of the following formulas:

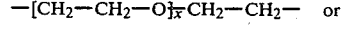
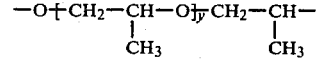

wherein x and y represent a whole number from 1 to 4 thereby representing a definite degree of polymerization or x and y can represent any number from 1 to 4 thereby representing an average degree of polymerization;

(b) the residue of a bis-secondary amino such as a derivative of piperazine having the formula:

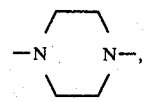

(c) the residue of a bis-primary amine of the formula —NH—Y—NH— wherein Y represents a linear or branched hydrocarbon or the bivalent radical, —$CH_2$—$CH_2$—S—S—$CH_2$—$CH_2$—, and (d) a ureylene group of the formula —NH—CO—NH—;

X is an anion such as chloride or bromide; and n is such that the molecular mass is between 1,000 and 100,000.

Polymers of this type are described, in particular, in French Pat. Nos. 2,320,330; 2,270,846; 76 20261; and 2,336,434 and U.S. Pat. Nos. 2,273,780; 2,375,853; 2,388,614; 2,454,547; 3,206,462; 2,261,002 and 2,271,378, all of which are incorporated herein by reference.

Other polymers of this type are described in U.S. Pat. Nos. 3,874,870; 4,001,432; 3,929,990; 3,966,904; 4,005,193; 4,025,617; 4,025,627; 4,025,653; 4,026,945 and 4,027,020, which are also incorporated herein by reference;

(3) crosslinked polyamino amides, optionally alkylated, which are selected from the group consisting of at least one water soluble crosslinked polymer obtained by crosslinking a polyamino-polyamide (A) prepared by polycondensing an acid compound with a polyamine. The acid compound is selected from (i) organic dicarboxylic acids, (ii) aliphatic mono- and di-carboxylic acids having two ethylenic links, (iii) esters of said acids and preferably the esters of lower alkanols having from 1 to 6 carbon atoms; and (iv) mixtures of these compounds. The polyamine is selected from bis-primary and mono- or di-secondary polyalkylene-polyamines. 0 to 40 mole percent of this polyamine can be replaced by a bis-primary amine, preferably ethylene diamine, or by a bis-secondary amine, preferably piperazine, and 0 to 20 mole percent can be replaced by hexamethylenediamine. The crosslinking is effected by means of a crosslinking agent (B) selected from eiphalohydrins, diepoxides, dianhydrides, unsaturated anhydrides, bis unsaturated derivatives. The crosslinking is effected by means of 0.025 to 0.35 mole of crosslinking agent per amine group of the polyamino-polyamide (A and generally from 0.025 to about 0.2, and in particular, from 0.025 to about 0.1 mole of crosslinking agent per amine group of the polyamino-polyamide (A). These polymers and their preparation are described in detail in French Pat. No. 2,252,840.

This crosslinked polymer is perfectly soluble in water at a concentration of 10% without formation of a gel. The viscosity of a 10% solution in water at 25° C. is greater than 3 centipoises and is generally between 3 and 200 centipoises.

The crosslinked and optionally alkylated polyaminoamides do not carry reactive groups, do not have alkylating properties and are chemically stable.

The polyaminoamides (A), per se, are also useful in accordance with the present invention;

(4) water-soluble crosslinked polyamino-amides obtained by crosslinking a polyamino-amide (A, described above) with a crosslinking agent selected from the group consisting of (I) a compound selected from the group consisting of (1) bis halohydrins, (2) bis azetidinium, (3) diamine bis haloacyls and (4) alkyl bis halides, (II) oligomers obtained by the reaction of a compound (a) selected from the group consisting of (1) bis halohydrins, (2) bis azetidinium, (3) diamine bis haloacyls, (4) alkyl bis halides, (5) epihalohydrins, (6) diepoxides, (7) bis unsaturated derivatives, with a compound (b) which is a bifunction compound reactive vis-a-vis compound (a), and (III) The product of the quaternization of a compound selected from the group consisting of compounds (a) and oligomers (II) and carrying one or more totally or partially alkylatable tertiary amine groups with an alkylating agent (c) selected from, preferably, the group consisting of methyl or ethyl chloride, bromide, iodide, sulfate, mesylate and tosylate, benzyl chloride or bromide, ethylene oxide, propylene oxide and glycidol, the crosslinking be effected by means of 0.025 to 0.35 mole, particularly 0.025 to 0.2 mole, and more particularly 0.025 to 0.1 mole of crosslinking agent per amine group of the polyamino-amide.

These crosslinking agents and these polymers as well as the process of preparing them are described in French Pat. No. 2,368,508, incorporated herein by reference;

(5) water-soluble polyamino-amide derivatives resulting from the condensation of a polyalkylene polyamine with a polycarboxylic acid which is then alkylated with a bifunctional agent obtained by reacting, in various molar proportions, epichlorohydrin with a secondary amine or a tertiary N,N'-alkylene diamine, the alkylene radical capable of being interrupted by a ureylene bridge, or a mixture of these amines in which the alkyl radical has 1–4 carbon atoms such as preferably, methyl, ethyl and propyl which are described in French Pat. No. 1,583,363.

The compounds which provide interesting results are copolymers of adipic acid and dimethylamino hydroxy propyl diethylenetriamine, sold under the trade name Cartaretine F, $F_4$ or $F_8$;

(6) polymers obtained by the reaction of a polyalkylene polyamine having two primary amine groups and at least one secondary amine group with a dicarboxylic acid selected from diglycolic acid, and saturated aliphatic dicarboxylic acids having 3–8 carbon atoms. The molar ratio of the polyalkylene polyamine and the dicarboxylic acid is between 0.8:1 and 1.4:1. The resulting polyamide is then reacted with epichlorohydrin. The molar ratio of epichlorohydrin relative to the secondary amine group of the polyamide is between 0.5:1 and 1.8:1. These polymers are disclosed in U.S. Pat. Nos. 3,227,615 and 2,961,347 which are also incorporated herein by reference.

Particularly interesting polymers are those sold under the trade name HERCOSETT 57 which has a viscosity at 25° C. of 30 cps in a 10% aqueous solution thereof; under the trade name PD 170 or DELSETTE 101 which are copolymers of adipic acid and epoxypropyl diethylenetriamine;

(7) polyalkylene-imines and in particular those polyethylene imines which are described in more detail in U.S. Pat. Nos. 2,182,306, 2,553,696, 2,806,839 and 2,208,085, as well as the alkylated or alkoxylated derivatives described in French Pat. Nos. 2,039,151 and 1,506,349.

Representative polyethylene imines and derivatives thereof include products sold under the trade names PEI 6; PEI 12; PEI 18; PEI 300; PEI 600; PEI 1200; PEI 1800; PEI 600E which is a polyethylene imine alkylated with ethylene oxide in a ratio of 1:0.75; TYDEX 14; and TYDEX 16 having a density of about 1.06 and a viscosity at 25° C. greater than 1000 cps. The various patents mentioned above are incorporated herein by reference.

Other polyethylene imines useful in accordance with the present invention are those sold under the trade names POLYMIN P having a density, $d_{20}$=about 1.07, a Brookfield viscosity of 10,000 to 20,000 cps in a 50% aqueous solution thereof (at 20° C. and 20 t/mn); PO- LYMIN SN, having a density, $d_{20}$=about 1.06, a viscosity of 800 to 1800 cps in a 20% aqueous solution thereof; POLYMIN HS, having a density, $d_{20}$=about 1.07 and a viscosity of 500 to 1,000 cps in a 20% aqueous solution thereof.

There can also be used in the present invention, the reaction product of polyethylene imine with ethyl formate, which is described in French Pat. No. 2,167,801; and (8) polymers containing in the chain thereof vinylpyridine or vinypyridinium units alone or combined together or with other units such as acrylamide, acrylamide substituted by, for example, an alkyl or alkylacrylate group. The nitrogen atom of the pyridinium group can carry a $C_1$–$C_{12}$ alkyl chain and the pyridine or pyridinium ring can, optionally, be substituted by 1–3 alkyl groups.

Representative of such polymers are the following:
(1) polyvinylpyridine,
(2) poly 1-butyl-4-vinyl pyridinium bromide,
(3) copolymer of 1-lauryl-4-vinyl pyridinium bromide and 1-butyl-4-vinyl pyridinium bromide,
(4) copolymer of 1-lauryl-4-vinyl pyridinium bromide and 1-ethyl-4-vinyl pyridinium bromide,
(5) copolymer of 2-vinylpyridine and 1-benzyl-2-methyl-5-vinylpyridinium chloride,
(6) copolymer of acrylamide and 1,2-dimethyl-5-vinylpyridinium methylsulfate,
(7) copolymer of methacrylamide and 1-benzyl-2-vinylpyridinium chloride,
(8) copolymer of methylmethacrylate and 1,2-dimethyl-5-vinylpyridinium methylsulfate and
(9) copolymer of ethylacrylate, 2-methyl 5-vinyl pyridine and 1,2-dimethyl 5-vinylpyridinium chloride.

Thus, the composition in accordance with the present invention comprises in an aqueous medium a fluorine derivative having anionic characteristics present in amounts between 0.01 and 10 percent by weight, and a cationic polymer in an amount between about 0.01 and 10 percent by weight and preferably between 0.05 and 5 weight percent of the said composition.

In addition to water, the composition of the present invention can also contain any other cosmetically acceptable solvent such as one selected from mono-alcohols, including alkanols having between 1–8 carbon atoms, for example, ethanol, isopropanol, benzyl alcohol and phenylethyl alcohol; polyalcohols such as alkylene glycols including ethylene glycol and propylene glycol; glycolethers such as the mono-, di- and tri-ethylene glycolmonoalkyl ethers, as for example, ethyleneglycolmonomethylether, ethyleneglycolmonoethylether and diethyleneglycolmonoethylether; esters such as ethyleneglycolmonomethylether acetate, ethyleneglycol monoethylether acetate, esters of fatty acids and lower alcohols, such as isopropyl myristate or palmitate; and methylene chloride. These solvents can be used separately or in admixture and are present, preferably, in amounts ranging between 5 and 70% by weight relative to the total weight of the composition.

The composition of the present invention can be provided in the form of a solution, a cream, a milk, a gel, a dispersion or an emulsion. It can also be packaged under pressure in an aerosol container together with an appropriate aerosol propellant.

The composition of the present invention can be utilized in various cosmetic operations and particularly those which include, conventionally, a rinsing operation. In the latter, the composition of the present invention gives some most surprising results.

The composition of this invention can, more particularly, be provided in the form of a shampoo, a treating cream which can be applied before or after a hair dyeing or bleaching operation, before or after a shampoo, or before or after a permanent wave operation. The composition can also be provided in the form of a hair dye product, a rinse lotion which can be applied before or after a shampoo, before or after a hair dyeing or bleaching operation, or before or after a permanent wave, and a hair setting or brushing lotion.

A preferred embodiment of the present invention comprises the use of the composition as a shampoo. This shampoo can contain, in addition to the fluorine derivative and the cationic polymer, at least one anionic, non-ionic, cationic or amphoteric surface active agent or a mixture thereof.

Representative anionic surface active agents include, in particular, the following compounds as well as mixtures thereof: alkaline salts, ammonium salts, amine salts or aminoalcohol salts of the following compounds: (1) alkylsulfates, alkylether sulfates, alkylamide sulfates, alkylamido ether sulfates, alkylarylpolyether sulfates and monoglyceride sulfates; (2) alkylsulfonates, alkyl amide sulfonates, alkylarylsulfonates and α-olefin sulfonates; (3) alkylsulfosuccinates, alkylethersulfosuccinates and alkylamide sulfosuccinates; (4) alkylsulfosuccinamates; (5) alkylsulfoacetates and alkylpolyglycerol carboxylates; (6) alkylphosphates and alkyletherphosphates; (7) alkylsarcosinates, alkylpolypeptidates, alkylamidopolypeptidates, alkylisethionates and alkyltaurates. The alkyl radical of all these compounds can be a linear chain having 12 to 18 carbon atoms; and (8) fatty acids such as oleic acid, ricinoleic acid, palmitic acid, stearic acid, the acids of copra oil or hydrogenated copra oil, carboxylic acids of polyglycol ethers having the formula

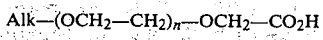
Alk—(OCH$_2$—CH$_2$)$_n$—OCH$_2$—CO$_2$H wherein Alk corresponds to a linear chain having from 12 to 18 carbon atoms and n is a whole number between 5 and 15.

Representative anionic surface active agents, which are those more particularly preferred, include: sodium lauryl sulfate, ammonium lauryl sulfate, triethanolamine lauryl sulfate, sodium laurylether sulfate oxyethylenated with 2.2 moles of ethylene oxide, the triethanolamine salt of keratinic lauroyl acid, the triethanolamine salt of the condensation product of copra acids and animal protein hydrolyzates and products of the formula: R—(OCH$_2$—CH$_2$)$_x$—OCH$_2$—COOH wherein R is generally alkyl having 12–14 carbon atoms and x ranges from 6 to 10.

Representative non-ionic surface active agents which can, optionally, be used in admixture with the above-mentioned anionic surface active agents, include the condensation products of a mono-alcohol, an α-diol, an alkylphenol, an amide or a diglycolamide with glycidol, such as, for example, a compound having the formula:

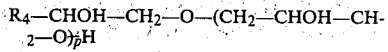
R$_4$—CHOH—CH$_2$—O—(CH$_2$—CHOH—CH$_2$—O)$_n$H wherein R$_4$ represents an aliphatic, cycloaliphatic or arylaliphatic radical having, preferably, between 7 and 21 carbon atoms, and mixtures thereof. The aliphatic chains can have ether, thioether or hydroxymethylene groups. The value of p in the above formula is between 1 and 10, inclusive. Such surface active agents are described in French Pat. No. 2,091,516. Other compounds include those having the formula

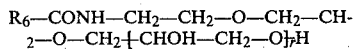

wherein $R_6$ represents a linear or branched, saturated or unsaturated, natural or synthetic, aliphatic radical or mixture thereof, optionally containing one or more hydroxy groups and having 8–30 carbon atoms; r represents a whole or decimal number from 1 to 5 which designates the average degree of condensation. Such compounds as are described in French Pat. No. 2,328,763.

There can also be employed compounds of the formula

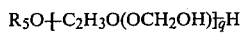

wherein $R_5$ represents alkyl, alkenyl or alkylaryl and q is a statistical value between 1 and 10, inclusive. Such compounds are as described in French Pat. No. 1,477,048.

Other compounds includable in this class are alcohols, alkylphenols, polyethoxylated or polyglycerolated fatty acids having a linear fatty chain having 8 to 18 carbon atoms and containing, most often, 2 to 30 moles of ethylene oxide. There can also be employed copolymers of ethylene oxide and propylene, condensates of ethylene oxide and propylene on fatty alcohols, polyethoxylated fatty amides, polyethoxylated fatty amines, ethanolamides, esters of fatty acids of glycol, esters of fatty acids of sorbitol and esters of fatty acids of sucrose.

Representative non-ionic surface active agents include those which are particularly preferred and which have the formula:

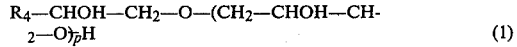 (1)

wherein $R_4$ represents a mixture of alkyl radicals having between 9 and 12 carbon atoms and p has a statistical value of 3.5;

 (2)

wherein $R_5$ represents $C_{12}H_{25}$ and q has a statistical value of 4 to 5; and

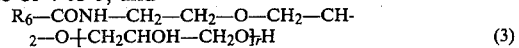 (3)

wherein $R_6$ represents a mixture of radicals derived from lauric, myristic, oleic and copra acids and r has a statistical value of 3 to 4.

The preferred oxyethylenated or polyglycerolated fatty alcohols are oleyl alcohol oxyethylenated with 10 moles of ethylene oxide, lauryl alcohol oxyethylenated with 12 moles of ethylene oxide, nonylphenol oxyethylenated with 9 moles of ethylene oxide, oleyl alcohol polyglycerolated with 4 moles of glycerol and sorbitan monolaurate polyoxyethylenated with 20 moles of ethylene oxide.

Representative cationic surface active agents which can be used alone or in admixture, include, particularly, salts of fatty amines, such as alkylamine acetates, quaternary ammonium salts such as alkyldimethylbenzylammonium chloride or bromide, alkyltrimethylammonium chloride or bromide, alkyldimethylhydroxyethylammonium chloride or bromide, dimethyldistearylammonium chloride or bromide, alkylamido ethyltrimethylammonium methosulfate, alkylpyridinium salts, and imidazoline derivatives. The alkyl radicals in these compounds have, preferably, between 1 and 22 carbon atoms. There can also be employed compounds having a cationic character such as amine oxides, including alkyldimethyl amine oxides or alkylaminoethyl dimethyl amine oxides.

Representative amphoteric surface active agents which can be used, include, more particularly, alkylamino, mono- and di-propionate of betaines, such as N-alkyl betaines, N-alkylsulfobetaines and N-alkylamidobetaines; cycloimidiniums such as alkylimidazolines; and asparagine derivatives. The alkyl group in these surface active agents have, preferably, between 1 and 22 carbon atoms.

In these shampoos, the amount of surface active agent is generally between 3 and 50 weight percent and, preferably, between 3 and 20 weight percent. The pH is generally between 3 and 10.

Another preferred embodiment comprises the use of a rinse lotion which is applied, principally, before or after a shampoo. These lotions can be an aqueous or hydroalcoholic solution, an emulsion or a thickened lotion.

When the composition is provided in the form of an emulsion, it can be non-ionic or anionic. The non-ionic emulsion comprises, principally, a mixture of oils and/or fatty alcohols and polyethoxylated fatty alcohols such as polyethoxylated stearyl or cetylstearyl alcohols. There can be added to these compositions cationic surface active agents such as, for example, those defined above.

Representative emulsions include those containing self-emulsifiable glycerine stearate sold under the trade name IMWITOR 960 K and a combination of glycerine monostearate with citric acid esters or indeed with fatty alcohols and lipopeptides or with alkaline stearates, sold respectively under the trade names LAMEFORM ZEM, PLM and NSM.

When the composition of the present invention is provided in the form of a gel, it can contain a thickening agent in the presence, or not, of a solvent. Useful thickening agents include sodium alginate or gum arabic or a cellulose derivative such as methyl cellulose, hydroxymethyl cellulose, hydroxyethyl cellulose, hydroxypropyl cellulose and hydroxypropylmethyl cellulose. Thickening of the lotion can also be achieved by employing polyethylene glycol, the stearate or distearate of polyethylene glycol or by using phosphoric esters and amides.

The amount of thickening agent can range from 0.05 to 30 weight percent and preferably from 0.5 to 15 weight percent of the composition. The pH of the rinsing lotion, also called a rinse, can range from 2 to 9.5.

The composition of the present invention can also be provided in the form of hair styling lotions, hair setting lotions, also called brushing lotions, and non-rinse lotions which are employed to reinforce a wave set.

These lotions include, generally, in an aqueous, alcoholic or hydroalcoholic solution, a combination of the above-defined components as well as, optionally, surface active agents such as non-ionic or cationic surface active agents, including those mentioned above.

When the composition of the present invention is pressurized in an aerosol container, there can be employed as the gaseous propellant, carbon dioxide, nitrogen, nitrous oxide, volatile hydrocarbons such as butane, isobutane, propane or preferably chlorinated or fluorinated hydrocarbons.

Obviously, the composition of the present invention can contain any other component conventionally used in cosmetics such as perfumes, dyes whose function is to color the composition itself, preservatives, sequesterants, thickening agents, softening agents, synergists, foam stabilizers, solar filters and peptizing agents. The choice of one or more of these conventional components will depend on the purpose for which the cosmetic is to be used.

The composition in accordance with the present invention can also contain other polymers and principally less substantive cationic polymers, anionic polymers such as those having acrylic acid, methacrylic acid, maleic acid, itaconic acid, fumaric acid, and crotonic acid units and their copolymers with ethylene derivatives, as well as amphoteric and non-ionic polymers.

The perfumes useful in these compositions are those which are cosmetically acceptable and they are present in an amount ranging, preferably, between 0.1 and 0.5 percent by weight of the composition.

A dye which is used to impart a color to the composition can be present in an amount of 0.001 to 0.5 percent by weight thereof.

When the composition in accordance with the present invention is to be applied to the skin, it can be provided in the form of a lotion, a cream, an emulsion, a gel, or a dispersion of the type mentioned above. Such a composition is principally used as an after-shave lotion, a toilet water, a shave foam or cream and a hand cream.

The process according to the present invention provides for the fixing of the above-named fluorine derivatives to the keratinic material by applying the said fluorine derivative to the keratinic material in combination with a substantive cationic polymer. It is understood that the said combination can also be effected on the keratinic material by initially applying a composition containing a cationic polymer, and then applying a composition comprising the fluorine derivative.

It is also possible to apply the compositions of the present invention in such a two-stage procedure where the compositions are provided in various forms and have different pH values. Such an operation avoids stability problems and favors the deposit of the active substance present in each composition.

As indicated above, formation of the combination of cationic polymer and fluorine derivative on keratinic material can be effected by applying in a first stage a composition containing the substantive cationic polymer, and then in a second stage applying a composition containing the fluorine derivative. These compositions can be used in various forms such as those defined above. For instance, a lotion can be employed in a first stage and then a shampoo in a second stage so as to obtain the desired effect.

The following non-limiting examples illustrate the present invention.

EXAMPLE 1

The following composition is prepared:

| | |
|---|---|
| Scotchban FC 807 | 0.4 g |
| Polyaminoamide, PAA-R1 | 0.6 g |
| Non-ionic surface active agent, TA-1 | 10 g |

-continued

| | |
|---|---|
| Lauric diethanolamide | 2 g |
| Water, sufficient for | 100 g |

The pH is adjusted to 6.7 with lactic acid.

This composition is used as a shampoo. Hair having an oily appearance is impregnated with this composition which provides a soft foam. The shampoo is permitted to remain in contact with the hair for 10 minutes after which the hair is rinsed and dried. The resulting dry hair is soft and flexible. Hair treated in this fashion takes on an oily appearance more slowly than hair treated with a conventional shampoo.

Similar results are achieved by applying, as indicated above, the compositions set forth in Examples 2-4:

EXAMPLE 2

The following composition is prepared:

| | |
|---|---|
| Scotchban FC 807 | 0.4 g |
| Cationic polymer, "CARTARETIN F 4" | 0.6 g |
| Non-ionic surface active agent, TA-1 | 10 g |
| Sodium $C_{12}$-$C_{14}$ alkyl ether sulfate, oxyethylenated with 2.2 moles of ethylene oxide | 10 g |
| Water, sufficient for | 100 g |

The pH is adjusted to 8.9 with monoethanolamine.

EXAMPLE 3

| | |
|---|---|
| Scotchban FC 807 | 0.4 g |
| Polymer, PAQ-2 | 0.4 g |
| Lauric diethanolamide | 1.5 g |
| Non-ionic surface active agent, TA-1 | 10 g |
| Water, sufficient for | 100 g |

The pH is adjusted to 6.7 with lactic acid.

EXAMPLE 4

| | |
|---|---|
| Scotchban FC 807 | 0.5 g |
| Merquat 550 | 0.5 g |
| Non-ionic surface active agent, T-1 | 10 g |
| Perfume, sufficient amount | |
| Dye, sufficient amount | |
| Water, sufficient for | 100 g |

The pH is adjusted to 6.7 with lactic acid.

Table 1, below, illustrates other compositions and variations of the present invention. It will be noted, as above, the re-appearance of an oily aspect of hair treated with these compositions is significantly delayed or retarded for a few days.

While this Table lists only the fluorine derivative, the cationic polymer, the surface active agent and the alkalizing agent or acidifying agent for adjustment of pH to the desired value it is to be understood that all the compositions include water in an amount to provide 100 g thereof. These compositions can also contain other cosmetic components such as preservatives, dyes and the like.

By replacing in Example 2 the polymer sold under the name CARTARETIN F4 by the polymer sold under the name CARTARETIN F8 or HERCOSETT 57 or PD 170, a good fixation of the fluorine derivative and a retardation of the reappearance of the oily appearance of the hair over a period of time are also achieved.

TABLE I
SHAMPOO COMPOSITIONS

| Ex. No. | Fluorine Derivative | Wt. (g) | Cationic Polymer | Wt. (g) | Surface Active Agent | Wt. (g) | pH | Acidifying Or Alkalizing Agent |
|---|---|---|---|---|---|---|---|---|
| 5 | SCOTCHBAN FC 807 | 0.5 | MERQUAT 550 | 0.6 | T A 1 | 10 | 5.5 | NaOH |
|   |   |   |   |   | Lauryl alcohol oxyethylenated with 12 moles of ethylene oxide | 5 |   |   |
| 6 | ZONYL FSA | 0.5 | Polymer PAA 1 | 0.5 | T A 1 | 10 | 9 | HCl |
| 7 | SCOTCHBAN FC 807 | 0.5 | Polymer PAA-R$_2$ | 0.5 | T A 1 | 10 | 9 | NaOH |
| 8 | " | 0.5 | Polymer PAA 1 | 0.5 | T A 1 | 10 | 9 | NaOH |
| 9 | FLUORAD FC 128 | 0.5 | Polymer PAQ 2 | 0.5 | T A 2 | 10 | 5.4 | NaOH |
| 10 | ZONYL FSA | 0.5 | Polymer PAA-R2 | 0.5 | T A 1 | 10 | 9 | NaOH |
| 11 | SCOTCHBAN FC 807 | 0.5 | Polymer PAA-R1 | 0.1 | T A 1 | 10 | 9 | NaOH |
| 12 | " | 0.2 | " | 0.2 | T A 1 | 10 | 9 | " |
| 13 | " | 0.5 | " | 0.5 | T A 1 | 10 | 9 | " |
| 14 | " | 0.5 | " | 0.5 | T A 1 | 5 | 9 | " |
| 15 | ZONYL FSA | 0.5 | POLYMIN P | 0.2 | T A 3 | 10 | 9 | HCl |
| 16 | ZONYL FSA | 0.5 | PAQ-3 | 0.5 | T A 1 | 10 | 5.3 | NaOH |
| 17 | ZONYL FSP | 0.5 | PAA-R2 | 0.5 | T A 1 | 10 | 8.5 | NaOH |
| 18 | ZONYL FSP | 0.5 | PAA-R1 | 0.5 | T A 1 | 10 | 9 | NaOH |
| 19 | ZONYL FSP | 0.5 | PAA-R1 | 0.5 | T A 1 | 10 | 8.6 | NaOH |
| 20 | ZONYL FSA | 0.5 | PAA-R2 | 0.5 | T A 1 | 3 | 9 | NaOH |
|   |   |   |   |   | SANDOPAN DTC | 10 |   |   |
| 21 | SCOTCHBAN FC 807 | 0.5 | PAA-R2 | 0.5 | T A 3 | 3 | 9 | NaOH |

EXAMPLE 22

| A - Shampoo containing | |
|---|---|
| Non-ionic surface active agent, TA-1 | 10 g |
| Polymer, PAA-R1 | 0.5 g |
| Water, sufficient for | 100 g |

The pH is adjusted to 7 with HCl.

| B - Lotion | |
|---|---|
| Scotchban FC 807 | 0.8 g |
| Water, sufficient for | 100 g |

The pH is adjusted to 7.5 with HCl.

The hair is washed with shampoo composition A, rinsed and then dried. The hair is then treated with lotion B, after which the hair is rinsed and dried. The hair thus treated does not have a tendency to take on an oily appearance even at the end of a few days.

The following examples illustrate other two-stage procedures, during the course of which the combination of the cationic polymer with the fluorine derivative is effected on the hair.

EXAMPLES 23 TO 26

By replacing the shampoo composition in Example 22 with shampoos having the following compositions and by proceeding in a manner similar to that indicated in Example 22, hair thus treated retains a non-oily appearance for a prolonged period of time:

| Ex. No. | Surface Active Agent | Amount (g) | Polymer | Amount (g) | pH | Acidifying Or Alkalizing Agent |
|---|---|---|---|---|---|---|
| 23 | TA-1 | 10 | Polymer PAQ-2 | 0.5 | 5 | HCl |
| 24 | TA-1 | 10 | Merquat 550 | 0.5 | 6.3 | NaOH |
| 25 | Akypo RLM 100 | 10 | Polymer PAA-R1 | 0.5 | 7.3 | HCl |
| 26 | Akypo RLM 100 | 10 | Polymer PAQ-2 | 0.5 | 6.2 | NaOH |

EXAMPLE 27

The following composition is prepared:

| C - Pre-shampoo lotion | |
|---|---|
| Polymer, PAA-R1 | 0.4 g |
| Water, sufficient for | 100 g |

The pH is adjusted to 8 with HCl.

| D - Shampoo composition | |
|---|---|
| Scotchban FC 807 | 0.5 g |
| Surface active agent, TA-2 | 10 g |
| Water, sufficient for | 100 g |

The pH is adjusted to 7.9 by NaOH.

Hair samples are treated with pre-shampoo lotion C and then dried. They are then washed with shampoo composition D, rinsed and dried.

Good results are also obtained by using the following compositions:

EXAMPLE 28

| E - Pre-shampoo lotion | |
|---|---|
| Polymer, PAQ-2 | 0.4 g |
| Water, sufficient for | 100 g |

The pH is adjusted to 6.5 with NaOH.

| F - Shampoo composition | |
|---|---|
| ZONYL FSA | 0.5 g |
| TA-1 | 10 g |
| Water, sufficient for | 100 g |

EXAMPLE 29

The following compositions are prepared:

| G - Pre-shampoo lotion | |
|---|---|
| Polymer, PAQ-3 | 0.6 g |
| Water, sufficient for | 100 g |
| The pH is adjusted to 7.8 with NaOH. | |
| H - Shampoo composition | |
| Scotchban FC 807 | 0.4 g |
| Lauryl alcohol oxyethylenated with 12 moles of ethylene oxide | 10 g |
| Water, sufficient for | 100 g |

The pH is adjusted to 3.5 with NaOH.

Hair samples are treated in the same manner as in Example 23. The resulting dry hair is soft and flexible and remains non-oily in appearance for an acceptable period of time.

EXAMPLE 30

The following composition is prepared:

| Scotchban FC 807 | 0.5 g |
|---|---|
| Polymer, PAA-R2 | 0.5 g |
| Surface active agent, TA-1 | 3 g |
| Water, sufficient for | 100 g |

The pH is adjusted to 9 with NaOH.

This composition is used as a rinse and is applied after shampooing the hair. This rinse is permitted to remain in contact with the hair for 10 minutes. The hair is then rinsed with water and dried. The hair thus treated exhibits softness, combs easily and remains non-oily in appearance for an acceptable period of time.

EXAMPLE 31

The following composition is prepared:

| Scotchban FC 807 | 0.2 g |
|---|---|
| Polymer, PAA-R1 | 0.6 g |
| Trimethylcetylammonium bromide | 0.1 g |
| Water, sufficient for | 100 g |

The pH is adjusted to 8.5 with 2-amino-2-methyl 1-propanol.

This composition is used as a hair setting lotion. After impregnating the hair with this lotion, the hair is rolled up on wave setting rollers and then dried. After removing the rollers, the hair is flexible, has a good hold for a prolonged period of time. Further, the hair remains non-oily in appearance for an acceptable period of time.

Similar results are obtained by using the following compositions:

EXAMPLE 32

| ZONYL FSA | 0.2 g |
|---|---|
| Polymer, PAA-R1 | 0.6 g |
| Trimethylcetylammonium bromide | 0.1 g |
| Water, sufficient for | 100 g |

The pH is adjusted to 8.5 with 2-amino-2-methyl-1propanol.

EXAMPLE 33

| ZONYL FSP | 0.4 g |
|---|---|
| Polymer, PAA-R1 | 0.6 g |
| Trimethylcetylammonium bromide | 0.2 g |
| Water, sufficient for | 100 g |

The pH is adjusted to 8.5 with 2-amino-2-methyl-1propanol.

The meaning of the various abbreviations and commercial names of components used in the preceding Examples are as follows:

Cationic Polymers

PAA-1: Polycondensate of equimolar amounts of adipic acid and diethylenetriamine.

PAA-R1: Polymer resulting from crosslinking polymer PAA-1 with epichlorohydrin (11 moles of epichlorohydrin per 100 amine groups).

PAA-R2: Polymer obtained by crosslinking polymer PAA-1 with a statistical oligomer crosslinking agent having the formula:

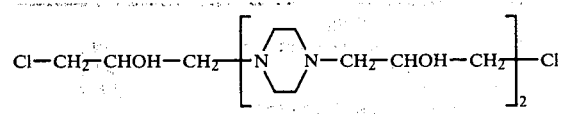

PAQ-1: Polymer having units of the formula:

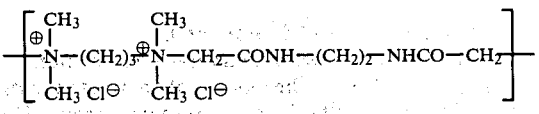

PAQ-2: Polymer having units of the formula:

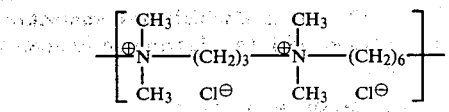

PAQ-3: Polymer having units of the formula:

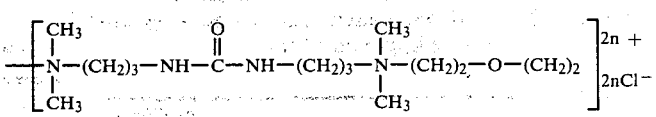

wherein n is equal to about 6.

Merquat 550: Copolymer of dimethyldiallyl ammonium chloride and acrylamide; MW ≥ 500,000.

Cartaretin F4: Copolymer of adipic acid-dimethylamino hydroxypropyl diethylene triamine.

Polymine P: Polyethyleneimine having a density $d_{20}$ = about 1.07, a Brookfield viscosity of 10,000–20,000 cps in 50% aqueous solution at 20° C. and 20 t/mn.

Florine Derivatives

Scotchban FC 807: Ammonium bis (N-2-ethyl-perfluoroalkylsulfonamidoethyl) phosphate, present in the form of a liquid comprising a solution in a mixture of isopropanol and water, 33% active material.

ZONYL FSA: Anionic fluorinated surface active agent in the form of a liquid comprising a solution in a mixture of isopropanol and water, 50% active material, flash point 42° C. (ASTMD-1310-17).

FLUORAD FC 128: Potassium fluoralkylated carboxylate present in the form of a powder, 100% active material.

Surface Active Agents

TA-1: R—CHOH+CH$_2$O—CH$_2$—CHOH—CH$_2$O$\overline{)_n}$H
wherein R=C$_9$-C$_{12}$ alkyl and n has a statistical value of 3.5.

AKYPO RLM 100: R—(OCH$_2$CH$_2$)$_z$ OCH$_2$COOH, wherein R is a mixture of C$_{12}$-C$_{14}$ alkyls and z is equal to 10.

SANDOPAN DTC: Sodium salt of 7-trideceth carboxylic acid of the formula: CH$_3$(CH$_2$)$_{11}$—CH$_2$—(OCH$_2$—CH$_2$)$_6$OCH$_2$—COOH.

TA-2: R—O+C$_2$H$_3$O(CH$_2$OH)$\overline{)_n}$H wherein R is C$_{12}$H$_{25}$ and n has a statistical value of 4 to 5.

TA-3: R—CO—NH—CH$_2$—CH$_2$—O—CH$_2$—CH$_2$—O+CH$_2$—CHOH—CH$_2$O$\overline{)_n}$H
wherein R is a mixture of radicals derived from lauric, myristic, oleic and copra acids and n has a statistical value of 3 to 4.

What is claimed is:

1. A cosmetic composition for use in the treatment of keratinic material including the hair and skin comprising in an aqueous medium
   (a) at least one fluorine derivative of the formula selected from the group consisting of (1) Gf—Z, (2) (GF—O)$_2$PO$_2$H, wherein Z represents —COOH, —SO$_3$H, —OSO$_3$H, —OPO$_2$H and —OPO$_3$H$_2$, and
   Gf represents a fluorinated radical of the formula

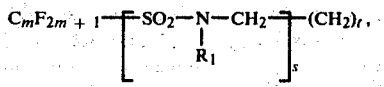

wherein m is 1-20, s is equal to 0 to 1, t is 0-20 and R$_1$ represents alkyl having 1-20 carbon atoms, with the proviso that when the fluorine derivative has the formula (Gf-O)$_2$PO$_2$H, the Gf moieties can be identical or different, and
   (3) the cosmetically acceptable salts of (1) and (2); and
   (b) at least one substantive cationic polymer having a significant number of tertiary or quaternary amine groups and a molecular weight between 500 and about 5,000,000, said substantive cationic polymer being selected from the group consisting of:
   (1) water soluble cyclopolymer having a molecular weight of 20,000 to 3,000,000 and having in the principal chain thereof units selected from the group consisting of

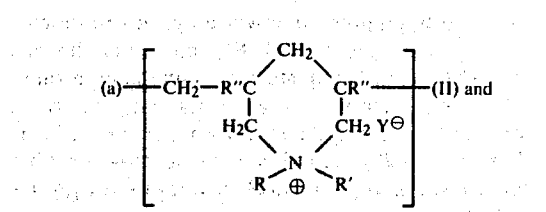

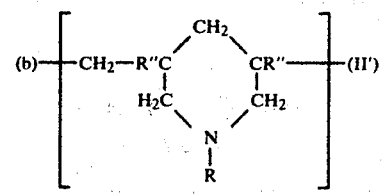

wherein
R" represents hydrogen or methyl,
R and R' each independently represent alkyl having 1-22 carbon atoms, hydroxyalkyl wherein the alkyl moiety has 1-5 carbon atoms, amido lower alkyl, or R and R' together with the nitrogen atom to which they are attached form piperidenyl or morpholinyl, and
Y$^\ominus$ represents an anion selected from the group consisting of bromide, chloride, acetate, borate, citrate, tartrate, bisulfate, bisulfite, sulfate and phosphate;
(1') copolymer of acrylamide having units of formula II or II' defined above;
(1") copolymer of diacetone acrylamide having units of formula II or II' defined above;
(2) a quaternary polyammonium having the formula:

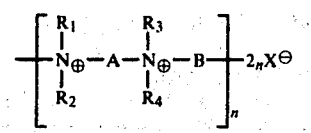

wherein R$_1$, R$_2$, R$_3$ and R$_4$ each independently represent an aliphatic, alicyclic or arylaliphatic radical containing a maximum of 20 carbon atoms, or lower hydroxy aliphatic radical; or the pairs R$_1$ and R$_2$, and R$_3$ and R$_4$, both or individually, taken with the nitrogen atoms to which each pair is attached form a heterocycle containing optionally a second heteroatom other than nitrogen, or R$_1$, R$_2$, R$_3$ and R$_4$ represent

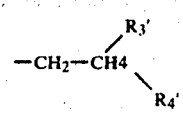

wherein R'$_3$ represents hydrogen or lower alkyl and R'$_4$ represents

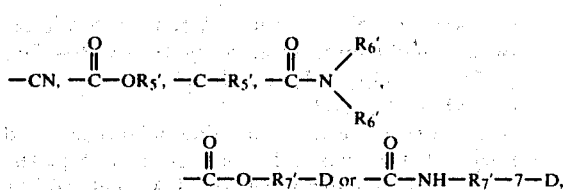

wherein $R'_5$ represents lower alkyl, $R'_6$ represents hydrogen or lower alkyl, $R'_7$ represents alkylene and D represents a quaternary ammonium group;

A and B represent (1") linear or branched, saturated or unsaturated polymethylene containing 2–20 carbon atoms, (2") the polymethylene of (4") having interposed in its principal chain one or more groups selected from

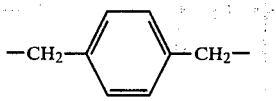

and —CH$_2$—Y—CH$_2$— wherein Y represents

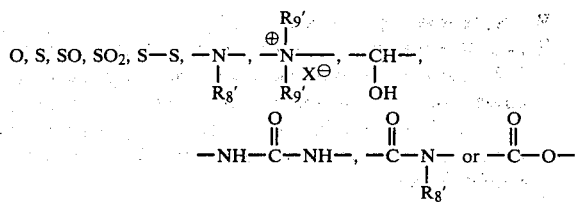

wherein $X^\ominus$ represents an anion derived from a mineral or organic acid, $R'_8$ represents hydrogen or lower alkyl and $R'_9$ represents lower alkyl, (3") A, $R_1$ and $R_3$ together with the nitrogen atoms to which $R_1$ and $R_3$ are attached form piperazine, or (4") when A represents linear or branched, saturated or unsaturated alkylene or hydroxyalkylene, B can represent —(CH$_2$)$_n$CO—D—OC—(CH$_2$)$_n$ wherein D represents
(i) the residue of a glycol of the formula —O—Z—O— where Z represents a linear or branched hydrocarbon or a group having a formula selected from —CH$_2$—CH$_2$—O—$_x$CH$_2$—CH$_2$— and

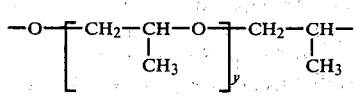

wherein x and y represent a whole number from 1 to 4 thereby representing a definite degree of polymerization or x and y represent any number from 1 to 4 thereby representing an average degree of polymerization,

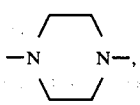

(iii) —NH—Y—NH— wherein Y represents a linear or branched hydrocarbon radical or —CH$_2$—CH$_2$—S—S—CH$_2$—CH$_2$—, and
(iv) —NH—CO—NH—;
X is an anion selected from chloride and bromide; and n is such that the molecular mass of the said quaternary polyammonium is between 1,000 and 100,000;
(3) a polyamino amide;

(4) a crosslinked polyamino amide selected from the group consisting of
(a) water soluble crosslinked polyamino amide obtained by crosslinking a polyamino amid prepared by polycondensing an acid with a polyamine, the crosslinking being effected with a crosslinking agent selected from the group consisting of an epihalohydrin, a diepoxide, a dianhydride, an unsaturated anhydride and a bis-unsaturated derivative, the amount of crosslinking agent comprises between 0.025 and 0.35 mole per amine group in said polyaminoamide,
(b) water soluble polyaminoamide obtained by crosslinking the polyaminoamide obtained as in (a) with a crosslinking agent selected from the group consisting of
(I) a compound selected from the group consisting of a bis halohydrin, a bis azetidinium, a diamine bis haloacyl and an alkyl bis halide,
(II) an oligomer obtained by reacting a compound selected from the group consisting of a compound of (I) defined above, an epihalohydrin, a diepoxide and a bis unsaturated derivative with a bifunctional compound reactive therewith, and
(III) the quaternization product of (a) a compound defined in I or (b) an oligomer defined in II above, having one or more totally of partially alkylatable tertiary amine groups with an alkylating agent, the crosslinking being effected by means of 0.025 to 0.35 mole of crosslinking agent per amine group of said polyaminoamide, and
(c) water soluble polyaminoamide derivatives resulting from the condensation of polyalkylene polyamines with polycarboxylic acids followed by an alkylation by bifunctional agents, obtained by reacting epichlorohydrin with secondary amines or tertiary N,N'-alkylene diamine, the alkylene chain being able to be interrupted by a ureylene group, or a mixture of these amines;
(5) polymer obtained by reacting a polyalkylene polyamine having two primary amine groups and at least one secondary amine group with a dicarboxylic acid selected from the group consisting of diglycolic acid and a saturated aliphatic dicarboxylic acid having 3–8 carbon atoms, the molar ratio of said polyalkylene polyamine to said dicarboxylic acid being between 0.8:1 and 1.4:1, the resulting polyamide being reacted with epichlorohydrin in a molar ratio of epichlorohydrin to secondary amine group of said polyamide between 0.5:1 and 1.8:1;
(6) polymer carrying in its chain vinylpyridine or vinylpyridinium units; and
(7) polyalkylene imines.

2. The composition of claim 1 wherein the fluorine derivative is selected from the group consisting of $C_7F_{15}$—COOH, $C_8F_{17}$—CH$_2$—COOH, $C_8F_{17}$—SO$_3$H, $$C_8F_{17}-SO_2-\underset{\underset{C_2H_5}{|}}{N}-(CH_2)_2-O-\overset{\overset{O}{\|}}{P}-(OH)_2,$$

$$[C_8F_{17}-SO_2-\underset{\underset{C_2H_5}{|}}{N}-(CH_2)_2-O]_{\overline{2}}\overset{\overset{O}{\|}}{P}-OH,$$

$$[C_{18}F_{37}-SO_2-\underset{\underset{C_2H_5}{|}}{N}-(CH_2)_{10}-CH_2-O]_{\overline{2}}\overset{\overset{O}{\|}}{P}-OH,$$

$$C_{12}F_{25}-SO_2-\underset{\underset{C_2H_5}{|}}{N}-(CH_2)_{10}-COOH \text{ and}$$

-continued

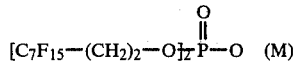 (M)

3. The composition of claim 1 which also includes at least one anionic, cationic, non-ionic or amphoteric surface active agent, or a mixture thereof.

4. The composition of claim 1 which also includes at least one solvent selected from the group consisting of a monoalcohol, a polyalcohol, glycol ether, ester of a fatty acid and a lower alcohol, an ester of a lower acid and glycol ether and methylene chloride.

5. The composition of claim 1 wherein said fluorine derivative having an anionic character is present in an amount of about 0.01 to 10 weight percent and said cationic polymer is present in an amount of about 0.01 to 10 weight percent of said composition.

6. The composition of claim 5 wherein both the said fluorine derivative and said cationic polymer are present in an amount of 0.05 to 5 percent by weight of said composition.

7. A cosmetic composition for use in the treatment of keratinic material including the hair and skin comprising in an aqueous medium
    (a) 0.01 to 10 weight percent of said composition of at least one fluorine derivative of the formula selected from the group consisting of (1) Gf—Z, (2) (Gf—O)$_2$PO$_2$H, wherein Z represents —COOH, —SO$_3$H, —OSO$_3$H, —OPO$_2$H and —OPO$_3$H$_2$ and Gf represents a fluorinated radical of the formula

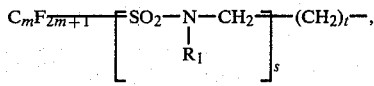

where m is 1–20, s is equal to 0 or 1, t is 0–20 and R$_1$ represents alkyl having 1–20 carbon atoms, with the proviso that when the fluorine derivative has the formula (Gf—O)$_2$PO$_2$H, the Gf moieties can be identical or different, and (3) the cosmetically acceptable salts of (1) and (2); and
    (b) about 0.01 to 10 weight percent of said composition of at least one substantive cationic polymer having a significant number of tertiary amine or quaternary amine groups and having a molecular weight between 500 and about 5,000,000, said cationic polymer providing a red color more intense than the control in the Rouge Supracide 3B test.

8. A process for treating keratinic material including the hair and skin comprising fixing thereon by means of a substantive cationic polymer having a significant number of tertiary or quaternary amine groups and a molecular weight between 500 and about 5,000,000 a fluorine compound selected from the group consisting of a compound having the formula Gf—Z and a compound having the formula (Gf—O)$_2$PO$_2$H, wherein Z represents —COOH, —SO$_3$H, —OSO$_3$H, —OPO$_2$H or —O-PO$_3$H$_2$ and Gf represents

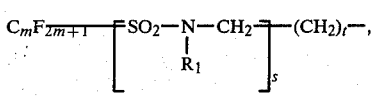

wherein m ranges from 1 to 20, s is 0 or 1, t ranges from 0 to 20 and R$_1$ represents alkyl having 1–20 carbon atoms with the proviso that when said fluorine derivative has the formula (Gf—O)$_2$PO$_2$H, the Gf moieties can be identical or different, said substantive cationic polymer being selected from the group consisting of:
(1) water soluble cyclopolymer having a molecular weight of 20,000 to 3,000,000 and having in the principal chain thereof units selected from the group consisting of

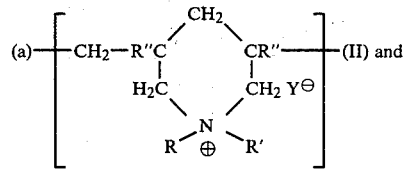

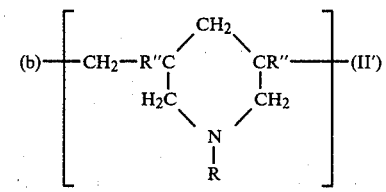

wherein
R" represents hydrogen or methyl,
R and R' each independently represent alkyl having 1–22 carbon atoms, hydroxyalkyl wherein the alkyl moiety has 1–5 carbon atoms, amido lower alkyl, or R and R' together with the nitrogen atom to which they are attached form piperidenyl or morpholinyl, and
Y$^\ominus$ represents an anion selected from the group consisting of bromide, chloride, acetate, borate, citrate, tartrate, bisulfate, bisulfite, sulfate and phosphate;
(1') copolymer of acrylamide having units of formula II or II' defined above;
(1") copolymer of diacetone acrylamide having units of formula II or II' defined above;
(2) a quaternary polyammonium having the formula:

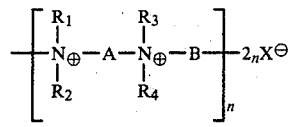

wherein R$_1$, R$_2$, R$_3$ and R$_4$ each independently represent an aliphatic, alicyclic or arylaliphatic radical containing a maximum of 20 carbon atoms, or lower hydroxy aliphatic radical; or the pairs R$_1$ and R$_2$, and R$_3$ and R$_4$, both or individually, taken with the nitrogen atoms to which each pair is attached form a heterocycle containing optionally a second heteroatom other than nitrogen, or R$_1$, R$_2$, R$_3$ and R$_4$ represent

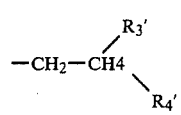

wherein R'$_3$ represents hydrogen or lower alkyl and R'$_4$ represents

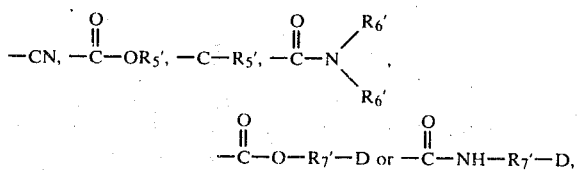

wherein $R'_5$ represents lower alkyl, $R'_6$ represents hydrogen or lower alkyl, $R'_7$ represents alkylene and D represents a quaternary ammonium group;

A and B represent (1″) linear or branched, saturated or unsaturated polymethylene containing 2–20 carbon atoms, (2″) the polymethylene of (1″) having interposed in its principal chain one or more groups selected from

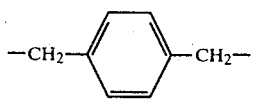

and —CH$_2$—Y—CH$_2$— wherein Y represents

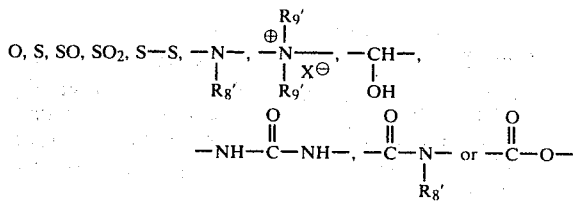

wherein $X^\ominus$ represents an anion derived from a mineral or organic acid, $R'_8$ represents hydrogen or lower alkyl and $R'_9$ represents lower alkyl, (3″) A, $R_1$ and $R_3$ together with the nitrogen atoms to which $R_1$ and $R_3$ are attached form piperazine, or (4″) when A represents linear or branched, saturated or unsaturated alkylene or hydroxyalkylene, B can represent —(CH$_2$)$_n$CO—D—OC—(CH$_2$)$_n$ wherein D represents (i) the residue of a glycol of the formula —O—Z—O— where Z represents a linear or branched hydrocarbon or a group having a formula selected from

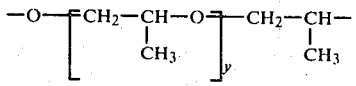

wherein x and y represent a whole number from 1 to 4 thereby representing a definite degree of polymerization or x and y represent any number from 1 to 4 thereby representing an average degree of polymerization, (ii)

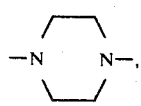

(iii) —NH—Y—NH— wherein Y represents a linear or branched hydrocarbon radical or —CH$_2$—CH$_2$—S—S—CH$_2$—CH$_2$—, and (iv) —NH—CO—NH—;

X is an anion selected from chloride and bromide; and n is such that the molecular mass of the said quaternary polyammonium is between 1,000 and 100,000;

(3) a polyamino amide;

(4) a crosslinked polyamino amide selected from the group consisting of (a) water soluble crosslinked polyamino amide obtained by crosslinking a polyamino amide prepared by polycondensing an acid with a polyamine, the crosslinking being effected with a crosslinking agent selected from the group consisting of an epihalohydrin, a diepoxide, a dianhydride, an unsaturated anhydride and a bis-unsaturated derivative, the amount of crosslinking agent comprises between 0.025 and 0.35 mole per amine group in said polyaminoamide, (b) water soluble polyaminoamide obtained by crosslinking the polyaminoamide obtained as in (a) with a crosslinking agent selected from the group consisting of (I) a compound selected from the group consisting of a bis halohydrin, a bis azetidinium, a diamine bis haloacyl and an alkyl bis halide, (II) an oligomer obtained by reacting a compound selected from the group consisting of a compound of (I) defined above, an epihalohydrin, a diepoxide and a bis unsaturated derivative with a bifunctional compound reactive therewith, and (III) the quaternization product of (a) a compound defined in I or (b) an oligomer defined in II above, having one or more totally or partially alkylatable tertiary amine groups with an alkylating agent, the crosslinking being effected by means of 0.025 to 0.35 mole of crosslinking agent per amine group of said polyaminoamide, and (c) water soluble polyaminoamide derivatives resulting from the condensation of polyalkylene polyamines with polycarboxylic acids followed by an alkylation by bifunctional agents, obtained by reacting epichlorohydrin with secondary amines or tertiary N,N'-alkylene diamine, the alkylene chain being able to be interrupted by a ureylene group, or a mixture of these amines;

(5) polymer obtained by reacting a polyalkylene polyamine having two primary amine groups and at least one secondary amine group with a dicarboxylic acid selected from the group consisting of diglycolic acid and a saturated aliphatic dicarboxylic acid having 3–8 carbon atoms, the molar ratio of said polyalkylene polyamine to said dicarboxylic acid being between 0.8:1 and 1.4:1, the resulting polyamide being reacted with epichlorohydrin in a molar ratio of epichlorohydrin to secondary amine group of said polyamide between 0.5:1 and 1.8:1;

(6) polymer carrying in its chain vinylpyridine or vinylpyridinium units; and (7) polyalkylene imines.

9. The process of claim 8 wherein said fluorine compound is fixed on said keratinic material with said substantive cationic polymer by applying to said keratinic material the composition of claim 1.

* * * * *